(12) United States Patent
Bonrath et al.

(10) Patent No.: US 9,040,742 B2
(45) Date of Patent: May 26, 2015

(54) CATALYTIC SYNTHESIS OF VITAMIN A INTERMEDIATE

(71) Applicant: DSM IP ASSETS B.V., Heerlen (NL)

(72) Inventors: Werner Bonrath, Kaiseraugst (CH); Bettina Wuestenberg, Kaiseraugst (CH); Thomas Netscher, Kaiseraugst (CH); Jan Schuetz, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/368,914

(22) PCT Filed: Dec. 14, 2012

(86) PCT No.: PCT/EP2012/075534
§ 371 (c)(1),
(2) Date: Jun. 26, 2014

(87) PCT Pub. No.: WO2013/098095
PCT Pub. Date: Jul. 4, 2013

(65) Prior Publication Data
US 2015/0031910 A1  Jan. 29, 2015

(30) Foreign Application Priority Data
Dec. 27, 2011 (EP) .................................... 11195785

(51) Int. Cl.
*C07C 67/29* (2006.01)
*C07C 69/00* (2006.01)

(52) U.S. Cl.
CPC ............. *C07C 67/29* (2013.01); *C07C 2101/16* (2013.01)

(58) Field of Classification Search
USPC .................................................. 560/220, 260
See application file for complete search history.

(56) References Cited

U.S. PATENT DOCUMENTS 5,424,478 A    6/1995  Tanaka et al.

FOREIGN PATENT DOCUMENTS

GB    1 034 189    6/1966

OTHER PUBLICATIONS

International Search Report for PCT/EP2012/075534 mailed Jan. 18, 2013.
R. José Garcia et al., "Unidirectional Thermal Electrocyclic Ring Forming Reactions of Methylenecyclobutenes from Vinylallenes in the Retinoid Series", Tetrahedron Letters, vol. 34, No. 39, Sep. 1, 1993, p. 6293-6296.

*Primary Examiner* — Sikarl Witherspoon
(74) *Attorney, Agent, or Firm* — Nixon & Vanderhye P.C.

(57) ABSTRACT

The present invention relates to a process of production of a compound, which is useful as an intermediate (building block) in organic synthesis, especially in the synthesis of vitamin A or β-carotene and derivatives thereof, e.g. canthaxanthin, astaxanthin or zeaxanthin.

11 Claims, No Drawings

CATALYTIC SYNTHESIS OF VITAMIN A INTERMEDIATE

This application is the U.S. national phase of International Application No. PCT/EP2012/075534 filed 14 Dec. 2012 which designated the U.S. and claims priority to EP 11195785.8 filed 27 Dec. 2011, the entire contents of each of which are hereby incorporated by reference.

The present invention relates to a process of production of a compound, which is useful as an intermediate (building block) in organic synthesis, especially in the synthesis of vitamin A or β-carotene and derivatives thereof, e.g. canthaxanthin, astaxanthin or zeaxanthin.

Vitamin A, which is represented by the following formula,

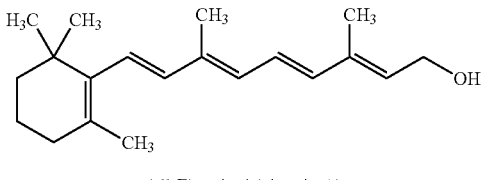

(all-E)-retinol (vitamin A)

is an important ingredient for many applications. Vitamin A plays a role in a variety of functions throughout the body, such as e.g. vision process, gene transcription, immune function, bone metabolism, haematopoiesis, skin and cellular health and antioxidant function.

Due to the importance of vitamin A (and its derivatives) and the complexity of the synthesis thereof, there is always a need for improved production processes.

The present invention relates to a synthesis, which allows a new way to produce compounds, which are useful for the production of vitamin A.

It was found that it is possible to produce a useful intermediate for the vitamin A production by a catalytic coupling reaction.

Therefore the present invention relates to a process of production of compounds of formula (I)

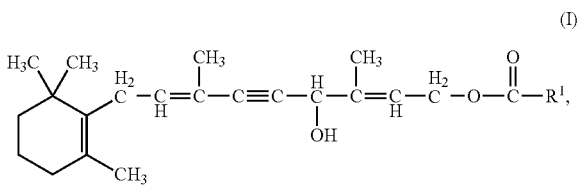

wherein $R^1$ signifies a $C_1$-$C_{15}$ alkyl moiety or a $C_2$-$C_{18}$ alkenyl moiety,
wherein a compound of formula (II)

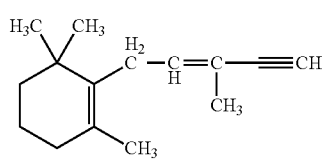

is reacted with a compound of formula (III)

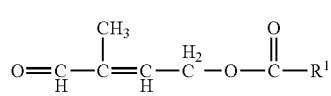

wherein $R^1$ has the same definition as for compound (I), and at least one organic nitrogen containing base, by using $Zn[SO_3CF_3]_2$ as catalyst.

$R^1$ signifies a $C_1$-$C_{15}$ alkyl moiety or a $C_2$-$C_{18}$ alkenyl moiety. When $R^1$ is a $C_1$-$C_{15}$ alkyl moiety, then preferably the alkyl moiety is linear. Especially preferred alkyl moieties are methyl, ethyl and pentadecyl. When $R^1$ is a $C_2$-$C_{18}$ alkenyl moiety, compound (I) can have more than three C—C double bonds. Preferably the alkenyl moiety is unbranched.

The process as described and claimed in the present patent application has many advantages.

First of all, it leads (in an easy and short way) to a compound, which is then used in the production of vitamin A.

The process according to the present invention is carried out with halogen free coupling components.

The process according to the present invention is a catalytic process. Therefore this method is superior to the commonly used stoichiometric coupling methods such as Grignard or Wittig reaction.

$Zn[SO_3CF_3]_2$ (Zinc triflat, also abbreviated as $Zn(OTf)_2$) is used as a catalyst. Zinc triflat does not react itself during the reaction and at the end of the reaction it can be recycled. Zinc triflat can be used in broad range of concentration catalytic amounts. Zinc triflat is usually used in an amount up to 20 molar percentages (mol-%) with regard to the mol of compound (II). It is also possible that higher amounts can be used.

Usually zinc triflat is used in an amount of 5 mol-% to 20 mol-% with regard to the mol of compound (II).

Therefore the present invention relates to a process of production of compounds of formula (I)

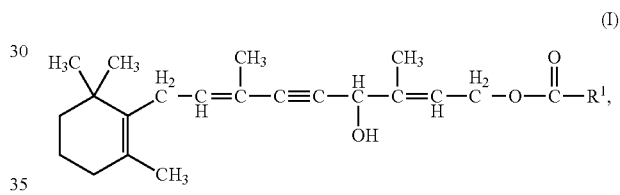

wherein $R^1$ signifies a $C_1$-$C_{15}$ alkyl moiety or a $C_2$-$C_{18}$ alkenyl moiety,
wherein a compound of formula (II)

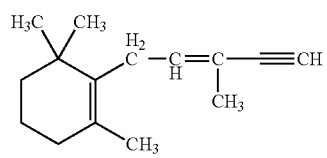

is reacted with a compound of formula (III)

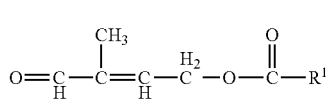

wherein $R^1$ has the same definition as for compound (I), and at least one organic nitrogen containing base, by using up to 20 mol-% of $Zn[OTf]_2$, with regard to the mol of compound (II), (preferably 5-20 mol-%, more preferably 10-20 mol-%).

Preferably $R^1$ is methyl, ethyl and pentadecyl.

The compound of formula (II), which is 1,3,3-trimethyl-2-(3-methylpent-2-en-4-ynyl)cyclohex-1-ene, can be in the E-form and/or in the Z-form.

1,3,3-trimethyl-2-(3-methylpent-2-en-4-ynyl)cyclohex-1-ene is usually obtained and used as a mixture of E- and Z-isomers. These forms do differ from each other by the position of the substituents of the C—C double bond in the side chain.

GB1034189 describes a method for the production of compound of formula (II) by dehydration of 3-methyl-5-(2,6,6-trimethylcyclohex-1-enyl)pent-1-yn-3-ol. A mixture of E/Z forms is obtained.

The compound of formula (III) (=3-methyl-4-oxobut-2-enyl acetate) can be synthesised by commonly known processes. It is also available commercially.

The process according to the present invention is carried out with at least one organic nitrogen containing base.

Suitable organic nitrogen containing bases are e.g. amines such as cyclic or acyclic amines, preferably tertiary amines, most preferably N,N-diisopropylethylamine, triethylamine and N,N-dicyclohexylmethylamine.

Therefore the present invention relates to a process of production of compounds of formula (I)

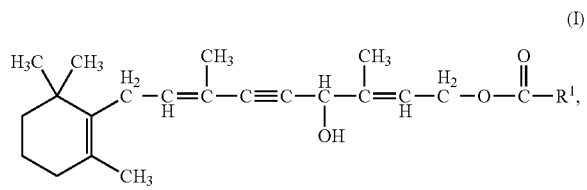

wherein $R^1$ signifies a $C_1$-$C_{15}$ alkyl moiety or a $C_2$-$C_{18}$ alkenyl moiety (preferably $R^1$ is methyl, ethyl or pentadecyl), wherein a compound of formula (II)

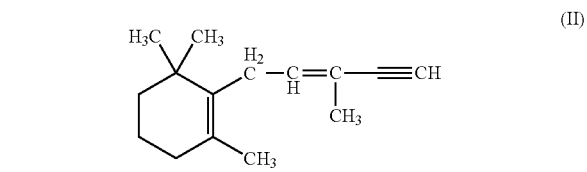

is reacted with a compound of formula (III)

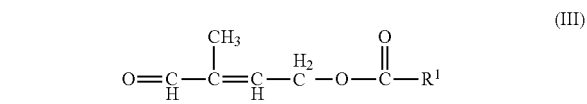

wherein $R^1$ has the same definition as for compound (I), and at least one cyclic or acyclic amine, (preferably at least one cyclic tertiary amine or acyclic tertiary amine, more preferably at least one tertiary amine chosen from the group consisting of N,N-diisopropylethylamine, triethylamine and N,N-dicyclohexylmethylamine) by using $Zn[SO_3CF_3]_2$ as catalyst.

The amount of the organic nitrogen containing base used in the process according to the present invention is usually up to 40 mol-%, with regard to the mol of compound (II) (preferably 5-40 mol-%, more preferably 10-40 mol-%).

Therefore the present invention relates to a process of production of compounds of formula (I)

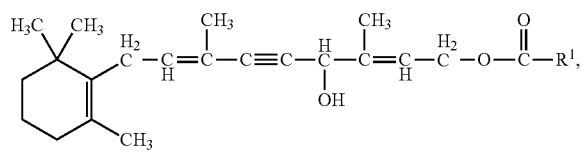

wherein $R^1$ signifies a $C_1$-$C_{15}$ alkyl moiety or a $C_2$-$C_{18}$ alkenyl moiety (preferably $R^1$ is methyl, ethyl or pentadecyl), wherein a compound of formula (II)

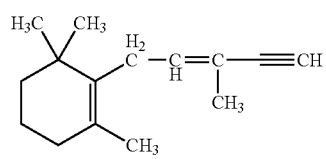

is reacted with a compound of formula (III)

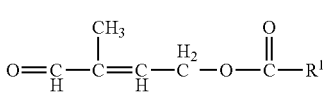

wherein $R^1$ has the same meaning as for compound (I)
and at least 5 mol-%, with regard to the mol of compound (II), of at least one organic nitrogen containing base chosen from the group consisting of N,N-diisopropylethylamine, triethylamine and N,N-dicyclohexylmethylamine, by using $Zn[OTf]_2$ as catalyst.

The process according to the present invention can be carried out with or without a solvent (or a mixture of solvents). Preferably at least one solvent is used. Preferably non-polar or polar aprotic solvents are used.

Suitable solvents are toluene, 1,2-dichloroethane, acetonitrile, N,N-diisopropylethylamine, dimethoxyethane (DME), tetrahydrofuran (THF), dioxane (=1,4-dioxane), cyclohexane, dichloromethane, diethyl ether, pentane, hexane, heptane, DMF, NMP and DMSO.

Preferred are polar aprotic solvents. Most preferred are acetonitrile, N,N-diisopropylethylamine and dimethoxyethane (DME).

Therefore the present invention relates to a process of production of compounds of formula (I)

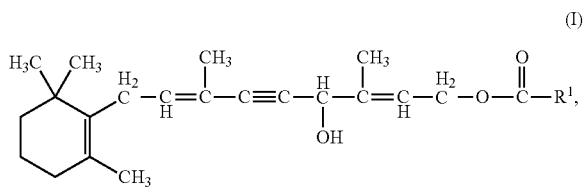

wherein $R^1$ signifies a $C_1$-$C_{15}$ alkyl moiety or a $C_2$-$C_{18}$ alkenyl moiety (preferably $R^1$ is methyl, ethyl or pentadecyl), wherein a compound of formula (II)

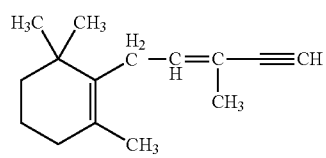

is reacted with a compound of formula (III)

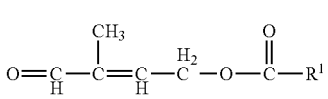

wherein $R^1$ has the same meaning as for compound (I) and up to 20 mol-%, in regard to the mol of compound (II), of at least one organic nitrogen containing base chosen from the group consisting of N,N-diisopropylethylamine, triethylamine and N,N-dicyclohexylmethylamine, by using $Zn[OTf]_2$ as catalyst, and wherein the process is carried out in acetonitrile, N,N-diisopropylethylamine or dimethoxyethane (DME) as a solvent.

The reaction is usually carried out at a temperature between 20 to 100° C.

Therefore the present invention relates to a process as described above wherein the process is carried out at a temperature between 20 to 100° C.

As already stated above, the advantage of this reaction is that it leads to a compound which is useful for the vitamin A production. The compounds of formula (I) can be converted into vitamin A derivatives by subsequent semi-hydrogenation, dehydration and isomerization.

The next process steps, which lead to the vitamin A can either been carried out directly with the product as obtained by the process according to the present invention or the product obtained by the process according to the present invention can be isolated and (if necessary) purified.

The obtained product can be isolated and purified using commonly known methods.

The following Examples serve to illustrate the invention. All parts are related to the weight and all temperatures are given in degree Celsius, when not otherwise stated.

EXAMPLES

Example 1

Under nitrogen atmosphere 74.2 mg (0.2 mmol) of zinc (II) triflate was transferred into a flame-dried 20 ml vial. The vial was sealed with a septum and outside the glove box an argon inlet was installed via syringe. Subsequently, 1.0 ml of anhydrous acetonitrile, 66 µl (0.4 mmol) of anhydrous N,N-diisopropylethylamine and 419 mg (2.0 mmol) of 1,3,3-trimethyl-2-(3-methylpent-2-en-4-ynyl)cyclohex-1-ene were added and the solution was stirred at 24° C. for 10 min. Then, 149 mg (1.0 mmol) of 3-methyl-4-oxobut-2-enyl acetate (compound of formula (III))

$$O=\underset{H}{C}-\underset{}{\overset{CH_3}{\underset{|}{C}}}=\underset{H}{C}-\overset{H_2}{C}-O-\overset{O}{\overset{\|}{C}}-R^1 \quad (III)$$

were added drop wise via syringe and the solution was heated to 60° C. in an aluminium heating block. After 4 h at 60° C. the orange solution was cooled to room temperature and 5 ml of saturated ammonium chloride solution and 5 ml of dichloromethane were added with intense stirring. The layers were separated and the aqueous layer was extracted with dichloromethane (3×5 ml). The combined organic extracts were dried over sodium sulphate, filtered and concentrated under reduced pressure (10 mbar) at 30° C. The product was obtained in 56% yield.

Example 2

Under nitrogen atmosphere 37.1 mg (0.1 mmol) of zinc (II) triflate was transferred into a flame-dried 20 ml vial. The vial was sealed with a septum and outside the glove box an argon inlet was installed via syringe. Subsequently, 0.2 ml of anhydrous acetonitrile, 33 µml (0.2 mmol) of anhydrous N,N-diisopropylethylamine and 419 mg (2.0 mmol) of 1,3,3-trimethyl-2-(3-methylpent-2-en-4-ynyl)cyclohex-1-ene were added and the solution was stirred at 24° C. for 10 min. Then, 149 mg (1.0 mmol) of 3-methyl-4-oxobut-2-enyl acetate (compound of formula (III))

$$O=\underset{H}{C}-\underset{}{\overset{CH_3}{\underset{|}{C}}}=\underset{H}{C}-\overset{H_2}{C}-O-\overset{O}{\overset{\|}{C}}-R^1 \quad (III)$$

were added drop wise via syringe and the solution was heated to 60° C. in an aluminium heating block. After 17.5 h at 40° C. the orange solution was cooled to room temperature and 5 ml of saturated ammonium chloride solution and 5 ml of dichloromethane were added with intense stirring. The layers were separated and the aqueous layer was extracted with dichloromethane (3×5 ml). The combined organic extracts were dried over sodium sulphate, filtered and concentrated under reduced pressure (10 mbar) at 30° C. The product was obtained in 59% yield.

Examples 3-4

The following examples have been carried out in analogy to example 1, with exception that the amount of the catalyst and/or the base and/or the amount of the base and/or the solvent has been varied.

| | Amount of Cat [mol-%] | Base | Amount of base [mol-%] | Solvent | Yield [%] |
|---|---|---|---|---|---|
| 3 | 10 | N,N-diisopropylethylamine | 20 | Acetonitril | 44.9 |
| 4 | 10 | N,N-diisopropylethylamine | 30 | Acetonitril | 34.6 |

Examples 5-8

Comparative Examples

All the following examples have been carried out in analogy to example 1 with exception that the catalyst and/or the base and/or the solvent has been varied.

| | Cat | Base | Solvent | Yield [%] |
|---|---|---|---|---|
| 5 | $Mg(OTf)_2$ | N,N-diisopropylethylamine | None | 0 |
| 6 | $Zn(NTf_2)_2$ | N,N-diisopropylethylamine | Acetonitril | 0 |
| 7 | $Bi(OTf)_2$ | N,N-diisopropylethylamine | DME | 2 |
| 8 | $ZnBr_2$ | N,N-diisopropylethylamine | DME | 5 |

It can be seen that the reaction does not work well (or not al all) with very similar catalytic compounds.

The invention claimed is:

1. A process for the production of compounds of formula (I):

(I)

[structure of compound I]

wherein $R^1$ signifies a $C_1$-$C_{15}$ alkyl moiety or a $C_2$-$C_{18}$ alkenyl moiety, wherein the process comprises reacting a compound of formula (II):

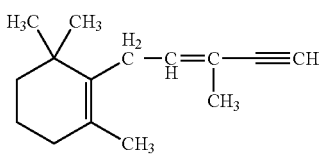

with a compound of formula (III):

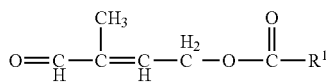

wherein $R^1$ has the same definition as for compound (I), and at least one organic nitrogen containing base, in the presence of $Zn[SO_3CF_3]_2$ as catalyst.

2. The process according to claim 1, wherein $R^1$ signifies methyl, ethyl and pentadecyl.

3. The process according to claim 1 wherein $R^1$ signifies an unbranched $C_2$-$C_{18}$ alkenyl moiety, which can have more than three C—C double bonds.

4. The process according to claim 1, wherein the $Zn[SO_3CF_3]_2$ catalyst is present in an amount of 5 mol-% to 20 mol-%, with regard to a molar amount of compound (II).

5. The process according to claim 1, wherein the organic nitrogen containing base is a cyclic amine or acyclic amine.

6. The process according to claim 1, wherein the organic nitrogen containing base is present in an amount up to 40 mol-%, with regard to a molar amount of compound (II).

7. The process according to claim 1, wherein the reaction is carried out in a non-polar or polar aprotic solvent.

8. The process according to claim 7, wherein the solvent is a polar aprotic solvent.

9. The process according to claim 1, wherein the reaction is carried out at a temperature between 20 to 100° C.

10. The process according to claim 5, wherein the organic nitrogen containing base is at least one tertiary amine.

11. The process according to claim 10, wherein the at least one tertiary amine is selected from the group consisting of N,N-diisopropylethylamine, triethylamine and N,N-dicyclohextylmethyl-amine.

* * * * *